(12) United States Patent
von Brasch et al.

(10) Patent No.: US 12,347,554 B2
(45) Date of Patent: *Jul. 1, 2025

(54) DYNAMIC VIRTUAL HEARING MODELLING

(71) Applicant: Cochlear Limited, Macquarie University (AU)

(72) Inventors: Alexander von Brasch, Cremorne (AU); Stephen Fung, Dundas Valley (AU)

(73) Assignee: Cochlear Limited, Macquarie University (AU)

( * ) Notice: Subject to any disclaimer, the term of this patent is extended or adjusted under 35 U.S.C. 154(b) by 130 days.

This patent is subject to a terminal disclaimer.

(21) Appl. No.: 18/346,971

(22) Filed: Jul. 5, 2023

(65) Prior Publication Data

US 2023/0352165 A1 Nov. 2, 2023

Related U.S. Application Data

(63) Continuation of application No. 17/294,098, filed as application No. PCT/IB2020/051398 on Feb. 19, 2020, now Pat. No. 11,735,318.

(Continued)

(51) Int. Cl.
*H04R 25/00* (2006.01)
*A61N 1/36* (2006.01)
*G16H 40/63* (2018.01)

(52) U.S. Cl.
CPC ......... *G16H 40/63* (2018.01); *A61N 1/36038* (2017.08); *H04R 25/505* (2013.01);
(Continued)

(58) Field of Classification Search
CPC .. A61N 1/36038; A61N 1/0541; G16H 40/63; G16H 40/67; G16H 50/50;
(Continued)

(56) References Cited

U.S. PATENT DOCUMENTS

| 8,755,533 B2 | 6/2014 | Banerjee et al. |
| 2009/0157143 A1 | 6/2009 | Edler et al. |

(Continued)

FOREIGN PATENT DOCUMENTS

| EP | 3281417 A1 | 2/2018 |
| WO | 2018/006979 A1 | 1/2018 |

OTHER PUBLICATIONS

EP 3 281 417 B1. "Systems and Method for Adjusting Auditory Prosthesis Settings" Andersson, Marcus. (Year: 2018).*

(Continued)

*Primary Examiner* — Brian Ensey
(74) *Attorney, Agent, or Firm* — Edell, Shapiro & Finnan, LLC

(57) ABSTRACT

Presented herein are techniques for generating, updating, and/or using a virtual hearing model associated with a recipient of an auditory prosthesis. The virtual hearing model is generated and updated for the recipient based on psychoacoustics data associated with the recipient and, in certain cases, based on psychoacoustics data gathered from one or more selected populations of auditory prosthesis recipients. The recipient-specific virtual hearing model can be used, in real-time, to determine one or more settings for the auditory prosthesis.

22 Claims, 7 Drawing Sheets

Related U.S. Application Data

(60) Provisional application No. 62/810,532, filed on Feb. 26, 2019.

(52) U.S. Cl.
CPC ....... *H04R 25/558* (2013.01); *H04R 2225/41* (2013.01); *H04R 2225/55* (2013.01); *H04R 2225/67* (2013.01)

(58) Field of Classification Search
CPC  H04R 25/505; H04R 25/558; H04R 2225/41; H04R 2225/55; H04R 2225/67
See application file for complete search history.

(56) References Cited

U.S. PATENT DOCUMENTS

| | | |
|---|---|---|
| 2011/0251704 A1 | 10/2011 | Walsh et al. |
| 2015/0215710 A1 | 7/2015 | Francart et al. |
| 2018/0110982 A1 | 4/2018 | Heasman et al. |
| 2018/0125415 A1 | 5/2018 | Reed et al. |
| 2018/0234776 A1 | 8/2018 | Fung et al. |
| 2018/0288541 A1 | 10/2018 | Chalupper et al. |
| 2019/0042189 A1 | 2/2019 | Torrini et al. |

OTHER PUBLICATIONS

International Search Report and Written Opinion in counterpart International Application No. PCT/IB2020/051398, mailed Jul. 8, 2020, 9 pages.

\* cited by examiner

693 — GENERATING, BASED ON RECIPIENT-SPECIFIC PSYCHOACOUSTICS DATA, A VIRTUAL HEARING MODEL, WHEREIN THE VIRTUAL HEARING MODEL IS HOLISTIC MODEL OF THE HEARING SYSTEM OF A RECIPIENT OF AN AUDITORY PROSTHESIS, AND WHEREIN THE VIRTUAL HEARING MODEL ACCOUNTS FOR, IN A BILATERAL MANNER, OPERATION OF EACH OF THE OUTER EARS, MIDDLE EARS, AND INNER EAR SYSTEMS OF THE RECIPIENT, AS WELL AS THE HEARING COGNITION IN AUDITORY CORTEX AND BRAIN OF THE RECIPIENT, AND HOW THE AUDITORY PROSTHESIS OPERATES AND THE PERCEPTION OF THE RECIPIENT

↓

694 — USING THE VIRTUAL HEARING MODEL TO DETERMINE SELECTED SOUND PROCESSING SETTINGS FOR USE BY THE AUDITORY PROSTHESIS

↓

695 — INSTANTIATING THE SELCTED SOUND PROCESSING SETTINGS AT THE AUDITORY PROSTHESIS

DYNAMIC VIRTUAL HEARING MODELLING

BACKGROUND

Field of the Invention

The present invention generally relates to auditory prostheses.

Related Art

Hearing loss is a type of sensory impairment that is generally of two types, namely conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain.

Individuals who suffer from conductive hearing loss typically have some form of residual hearing because the hair cells in the cochlea are undamaged. As such, individuals suffering from conductive hearing loss typically receive an auditory prosthesis that generates motion of the cochlea fluid. Such auditory prostheses include, for example, acoustic hearing aids, bone conduction devices, and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical and the like). Cochlear implants are often proposed when the sensorineural hearing loss is due to the absence or destruction of the cochlea hair cells, which transduce acoustic signals into nerve impulses. An auditory brainstem stimulator is another type of stimulating auditory prosthesis that might also be proposed when a recipient experiences sensorineural hearing loss due to damage to the auditory nerve.

SUMMARY

In one aspect, a method is provided. The method comprises: receiving, from an auditory prosthesis configured to be worn by a recipient, a request for updated sound processing settings, wherein the request includes listening situation data representing an expected listening situation for the auditory prosthesis; determining, based on a recipient-specific virtual hearing model accounting for how the auditory prosthesis operates and aids the perception of the recipient, selected sound processing settings for use by the auditory prosthesis in the expected listening situation; and sending the selected sound processing settings to the auditory prosthesis.

In another aspect, a method is provided. The method comprises: generating, based on recipient-specific psychoacoustics data, a virtual hearing model, wherein the virtual hearing model is holistic model of the hearing system of a recipient of an auditory prosthesis, and wherein the virtual hearing model accounts for, in a bilateral manner, operation of each of the outer ears, middle ears, and inner ear systems of the recipient, as well as the hearing cognition in auditory cortex and brain of the recipient, and how the auditory prosthesis operates and aids the perception of the recipient; using the virtual hearing model to determine selected sound processing settings for use by the auditory prosthesis; and instantiating the selected sound processing settings at the auditory prosthesis.

BRIEF DESCRIPTION OF THE DRAWINGS

Embodiments of the present invention are described herein in conjunction with the accompanying drawings, in which:

FIG. 6 is a flowchart of a method, in accordance with certain embodiments presented herein.

DETAILED DESCRIPTION

Presented herein are techniques for generating, updating, and/or using a virtual hearing model associated with a recipient of an auditory prosthesis. The virtual hearing model is generated and updated for the recipient based on psychoacoustics data associated with the recipient and, in certain cases, based on psychoacoustics data gathered from one or more selected populations of auditory prosthesis recipients. The recipient-specific virtual hearing model can be used, in real-time, to determine one or more settings for the auditory prosthesis.

Merely for ease of description, the techniques presented herein are primarily described herein with reference to one illustrative auditory/hearing prosthesis, namely a cochlear implant. However, it is to be appreciated that the techniques presented herein may also be used with a variety of other types of devices, including other auditory prostheses. For example, the techniques presented herein may be implemented in, for example, acoustic hearing aids, auditory brainstem stimulators, bone conduction devices, middle ear auditory prostheses, direct acoustic stimulators, bimodal auditory prosthesis, bilateral auditory prosthesis, etc. As such, description of the invention with reference to a cochlear implant should not be interpreted as a limitation of the scope of the techniques presented herein.

Figure 1A:
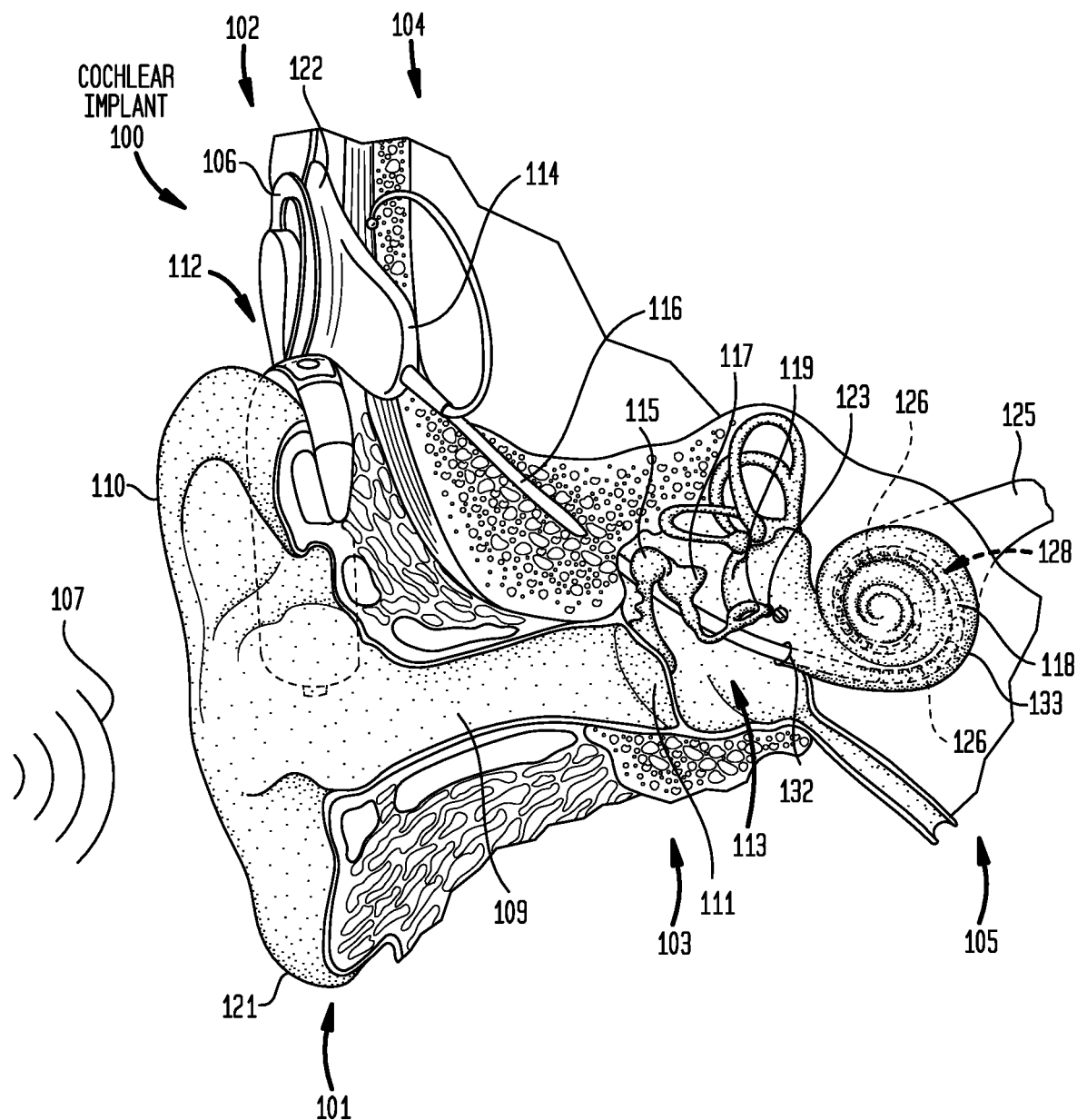
FIG. 1A is a schematic diagram illustrating a cochlear implant, in accordance with certain embodiments presented herein.
Figure 1B:
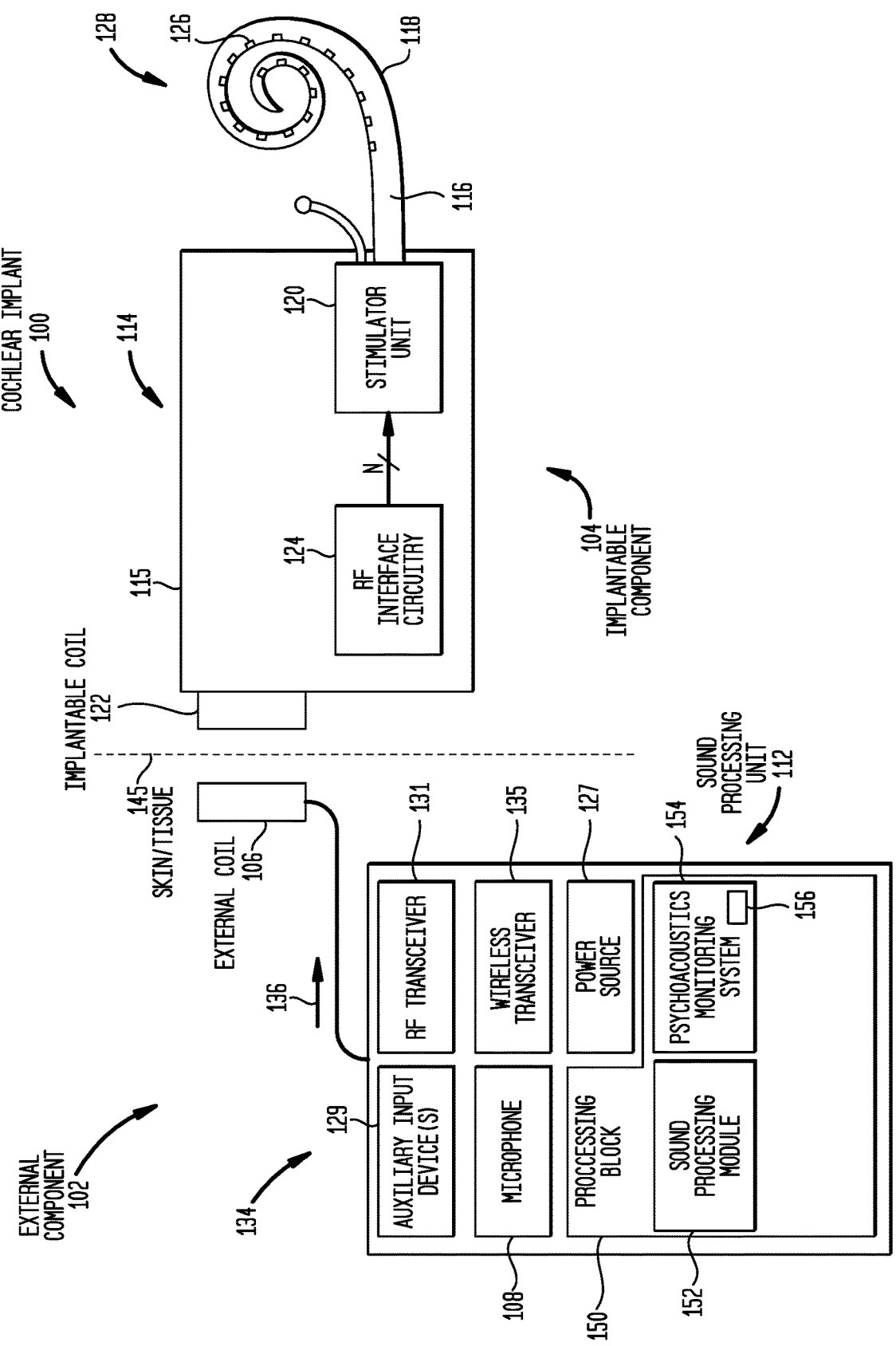
FIG. 1B is a block diagram of the cochlear implant of FIG. 1A.

FIG. 1A is ab schematic diagram of an exemplary cochlear implant 100 configured to implement aspects of the techniques presented herein, while FIG. 1B is a block diagram of the cochlear implant 100. For ease of illustration, FIGS. 1A and 1B will be described together.

As shown, the recipient has an outer ear 101, a middle ear 103 and an inner ear 105. Elements of outer ear 101, middle ear 103 and inner ear 105 are described below, followed by a description of cochlear implant 100.

In a fully functional human hearing anatomy, outer ear 101 comprises an auricle 121 and an ear canal 109. A sound wave or acoustic pressure 107 is collected by auricle 121 and channeled into and through ear canal 109. Disposed across the distal end of ear canal 109 is a tympanic membrane 111 which vibrates in response to acoustic wave 107. This vibration is coupled to oval window or fenestra ovalis 123 through three bones of middle ear 103, collectively referred to as the ossicles 113 and comprising the malleus 115, the incus 117 and the stapes 119. The ossicles 113 of middle ear 103 serve to filter and amplify acoustic wave 107, causing oval window 123 to vibrate. Such vibration sets up waves of fluid motion within cochlea 133. Such fluid motion, in turn, activates hair cells (not shown) that line the inside of cochlea 133. Activation of the hair cells causes appropriate nerve impulses to be transferred through the spiral ganglion cells and auditory nerve 125 to the brain (not shown), where they are perceived as sound.

The cochlear implant 100 comprises an external component 102 and an internal/implantable component 104. The external component 102 is directly or indirectly attached to the body of the recipient and typically comprises an external coil 106 and, generally, a magnet (not shown in FIG. 1) fixed relative to the external coil 106. The external component 102 also comprises one or more input elements/devices 134 for receiving input signals at a sound processing unit 112. In this example, the one or more input devices 134 include a plurality of microphones 108 (e.g., microphones positioned by auricle 110 of the recipient, telecoils, etc.) configured to capture/receive input acoustic/sound signals (sounds), one or more auxiliary input devices 129 (e.g., a telecoil, one or more audio ports, such as a Direct Audio Input (DAI), a data port, such as a Universal Serial Bus (USB) port, cable port, etc.), and a wireless transmitter/receiver (transceiver) 135, each located in, on, or near the sound processing unit 112.

The sound processing unit 112 also includes, for example, at least one battery 127, a radio-frequency (RF) transceiver 131, and a processing block 150. The processing block 150 comprises a number of elements, including a sound processing module 152 and a psychoacoustics monitoring system 154. As described further below, in certain embodiments the psychoacoustics monitoring system 154 includes an environmental classifier 156. Each of the sound processing module 152 and the psychoacoustics monitoring system 154 may be formed by one or more processors (e.g., one or more Digital Signal Processors (DSPs), one or more uC cores, etc.), firmware, software, etc. arranged to perform operations described herein. That is, the sound processing module 152 and the psychoacoustics monitoring system 154 may each be implemented as firmware elements, partially or fully implemented with digital logic gates in one or more application-specific integrated circuits (ASICs), partially or fully in software, etc.

As described further below, the psychoacoustics monitoring system 154 is configured to, in certain examples, monitor or analyze sound signals received at the one or more input devices 134. More specifically, the psychoacoustics monitoring system 154 may be configured to capture, extract, determine, or otherwise obtain recipient-specific psychoacoustics data from the sound signals for use in generating or updating a recipient-specific virtual hearing model for the recipient. Additionally or alternatively, also as described below, the psychoacoustics monitoring system 154 may be configured to initiate a request for updated settings, such as updated sound processing settings, for the cochlear implant 100. The request for updated settings may include so-called listening situation data representing an expected listening situation for the recipient of cochlear implant 100. The listening situation data is generated, by the psychoacoustics monitoring system 154, from the sound signals received at the one or more input devices 134. Further details of the psychoacoustics monitoring system 154, which is on-board (i.e., integrated in) cochlear implant 100, are provided below.

As noted, in certain embodiments, the psychoacoustics monitoring system 154 may include an environmental classification module (environmental classifier) 156 that is configured to evaluate/analyze the received sound signals (sounds) and determine the sound class/category/environment of the sounds. That is, the environmental classifier 156 is configured to use the received sounds to "classify" the ambient sound environment and/or the sounds into one or more sound categories (i.e., determine the input signal type). The sound class or environment may include, but are not limited to, "Speech" (e.g., the sound signals include primarily speech signals), "Noise" (e.g., the sound signals include primarily noise signals), "Speech+Noise" (e.g., both speech and noise are present in the sound signals), "Wind" (e.g., the sound signals include primarily wind signals), "Music" (e.g., the sound signals include primarily music signals), and "Quiet" (e.g., the sound signals include minimal speech or noise signals). The environmental classifier 156 may also estimate the signal-to-noise ratio (SNR) of the sounds.

Returning to the example embodiment of FIGS. 1A and 1B, the implantable component 104 comprises an implant body (main module) 114, a lead region 116, and an intra-cochlear stimulating assembly 118, all configured to be implanted under the skin/tissue (tissue) 145 of the recipient. The implant body 114 generally comprises a hermetically-sealed housing 115 in which RF interface circuitry 124 and a stimulator unit 120 are disposed. The implant body 114 also includes an internal/implantable coil 122 that is generally external to the housing 115, but which is connected to the RF interface circuitry 124 via a hermetic feedthrough (not shown in FIG. 1B).

As noted, stimulating assembly 118 is configured to be at least partially implanted in the recipient's cochlea 133. Stimulating assembly 118 includes a plurality of longitudinally spaced intra-cochlear electrical stimulating contacts (electrodes) 126 that collectively form a contact or electrode array 128 for delivery of electrical stimulation (current) to the recipient's cochlea. Stimulating assembly 118 extends through an opening in the recipient's cochlea (e.g., cochleostomy, the round window, etc.) and has a proximal end connected to stimulator unit 120 via lead region 116 and a hermetic feedthrough (not shown in FIG. 1B). Lead region 116 includes a plurality of conductors (wires) that electrically couple the electrodes 126 to the stimulator unit 120.

As noted, the cochlear implant 100 includes the external coil 106 and the implantable coil 122. The coils 106 and 122 are typically wire antenna coils each comprised of multiple turns of electrically insulated single-strand or multi-strand platinum or gold wire. Generally, a magnet is fixed relative to each of the external coil 106 and the implantable coil 122. The magnets fixed relative to the external coil 106 and the implantable coil 122 facilitate the operational alignment of the external coil with the implantable coil. This operational alignment of the coils 106 and 122 enables the external component 102 to transmit data, as well as possibly power, to the implantable component 104 via a closely-coupled wireless link formed between the external coil 106 with the implantable coil 122. In certain examples, the closely-coupled wireless link is a radio frequency (RF) link. However, various other types of energy transfer, such as infrared (IR), electromagnetic, capacitive and inductive transfer, may be used to transfer the power and/or data from an external component to an implantable component and, as such, FIG. 1B illustrates only one example arrangement.

As noted above, the processing block 150 includes sound processing module 152. The sound processing module 152 (e.g., one or more processing elements implementing firmware, software, etc.) is configured to, in general, convert input sound signals into stimulation control signals 136 for use in stimulating a first ear of a recipient (i.e., the sound processing module 152 is configured to perform sound processing on input sound signals received at the one or more input devices 134 to generate signals 136 that represent electrical stimulation for delivery to the recipient). The input sound signals that are processed and converted into stimulation control signals may be audio signals received via the microphones 108 or any of the other input devices 134.

In the embodiment of FIG. 1B, the stimulation control signals 136 are provided to the RF transceiver 131, which transcutaneously transfers the stimulation control signals 136 (e.g., in an encoded manner) to the implantable component 104 via external coil 106 and implantable coil 122. That is, the stimulation control signals 136 are received at the RF interface circuitry 124 via implantable coil 122 and provided to the stimulator unit 120. The stimulator unit 120 is configured to utilize the stimulation control signals 136 to generate electrical stimulation signals (e.g., current signals) for delivery to the recipient's cochlea via one or more stimulating contacts 126. In this way, cochlear implant 100 electrically stimulates the recipient's auditory nerve cells, bypassing absent or defective hair cells that normally transduce acoustic vibrations into neural activity, in a manner that causes the recipient to perceive one or more components of the input audio signals.

FIGS. 1A and 1B illustrate an arrangement in which the cochlear implant 100 includes an external component. However, it is to be appreciated that embodiments of the present invention may be implemented in cochlear implants having alternative arrangements. For example, elements of the sound processing unit 112 (e.g., such as the processing block 150, power source 102, etc.), may be implanted in the recipient.

It is also to be appreciated that the individual components referenced herein, e.g., microphones 108, auxiliary inputs 129, processing block 150, etc., may be distributed across more than one prosthesis, e.g., two cochlear implants 100, and indeed across more than one type of device, e.g., cochlear implant 100 and a consumer electronic device or a remote control of the cochlear implant 100.

As noted, the sound processing module 152 is configured to convert input sound signals into stimulation control signals 136 for use in stimulating a first ear of a recipient. The sound processing module 152 processes the sound signals in accordance with various operating parameters dictated by one of a number of selectable settings or modes of operation. The various selectable settings or modes of operation may be in the form of executable programs or sets of parameters for use in a program. The settings may accommodate any of a number of specific configurations that influence the operation of the cochlear implant. For example, the settings may include different digital signal and sound processing algorithms, processes and/or operational parameters for different algorithms, other types of executable programs (such as system configuration, user interface, etc.), or operational parameters for such programs. In certain examples, the selectable settings would be stored in a memory of the cochlear implant 100 and relate to different optimal settings for different listening situations or environments encountered by the recipient (i.e., noisy or quite environments, windy environments, etc.).

Additionally, since the dynamic range for electrical stimulation is relatively narrow and varies across recipients and stimulating contacts, programs used in sound processing module 152 may be individually tailored to optimize the perceptions presented to the particular recipient (i.e., tailor the characteristics of electrical stimulation for the recipient). For example, many speech processing strategies rely on a customized set of stimulation settings which provide, for a particular recipient, the threshold levels (T-levels) and comfortable levels (C-levels) of stimulation for each frequency band. Once these stimulation settings are established, the sound processor may then optimally process and convert the received acoustic signals into stimulation data for use by the stimulator unit 120 in delivering stimulation signals to the recipient.

As such, it is clear that a typical cochlear implant has many parameters which determine the sound processing operations of the device. The individualized programs, commands, data, settings, parameters, instructions, modes, and/or other information that define the specific characteristics used by cochlear implant 100 to process electrical input signals and generate stimulation data therefrom are generally and collectively referred to as the recipient's "MAP" or, more generally, the cochlear implant or auditory prosthesis "sound processing settings." As described further below, presented herein are techniques for selecting and/or dynamically adjusting, potentially in real-time, the sound processing settings of an auditory prosthesis, such as cochlear implant 100, based on a recipient-specific (individualized) "virtual hearing model."

As used herein, a recipient-specific or individualized "virtual hearing model" is an advanced and customized computing model representing the complete or holistic operation of the hearing system of the recipient of an auditory prosthesis. That is, the recipient-specific virtual hearing model is able to receive, as inputs, representations of sounds and then estimate how the recipient would "perceive" those represented sounds (i.e., what the recipient would likely hear if those sounds were input to the recipient's actual ear). As described further below, the recipient-specific virtual hearing model can be used in advanced computer simulations to determine, potentially in real-time, optimal sound processing settings (e.g., algorithms, programs, etc.) for an auditory prosthesis, thereby improving the recipient's hearing perception. The recipient-specific virtual hearing model can be used in to plan customized rehabilitation exercises for the recipient.

In accordance with embodiments presented herein, a recipient-specific virtual hearing model is a holistic model of the hearing system of the recipient, meaning that the model covers (accounts for) each of the outer ear, middle ear, and inner ear systems, as well as some element of the hearing cognition in auditory cortex and brain, in a bilateral manner (i.e., accounts for both ears of the recipient). The recipient-specific virtual hearing model also accounts for how the auditory prosthesis (e.g., cochlear implant 100) operates and aids the perception of the recipient. As described further below, a recipient-specific virtual hearing model is generated based on recipient-specific data/information, sometimes referred to herein as recipient-specific psychoacoustics data, and, potentially, data gathered from one or more selected populations of auditory prosthesis recipients.

Figure 2:
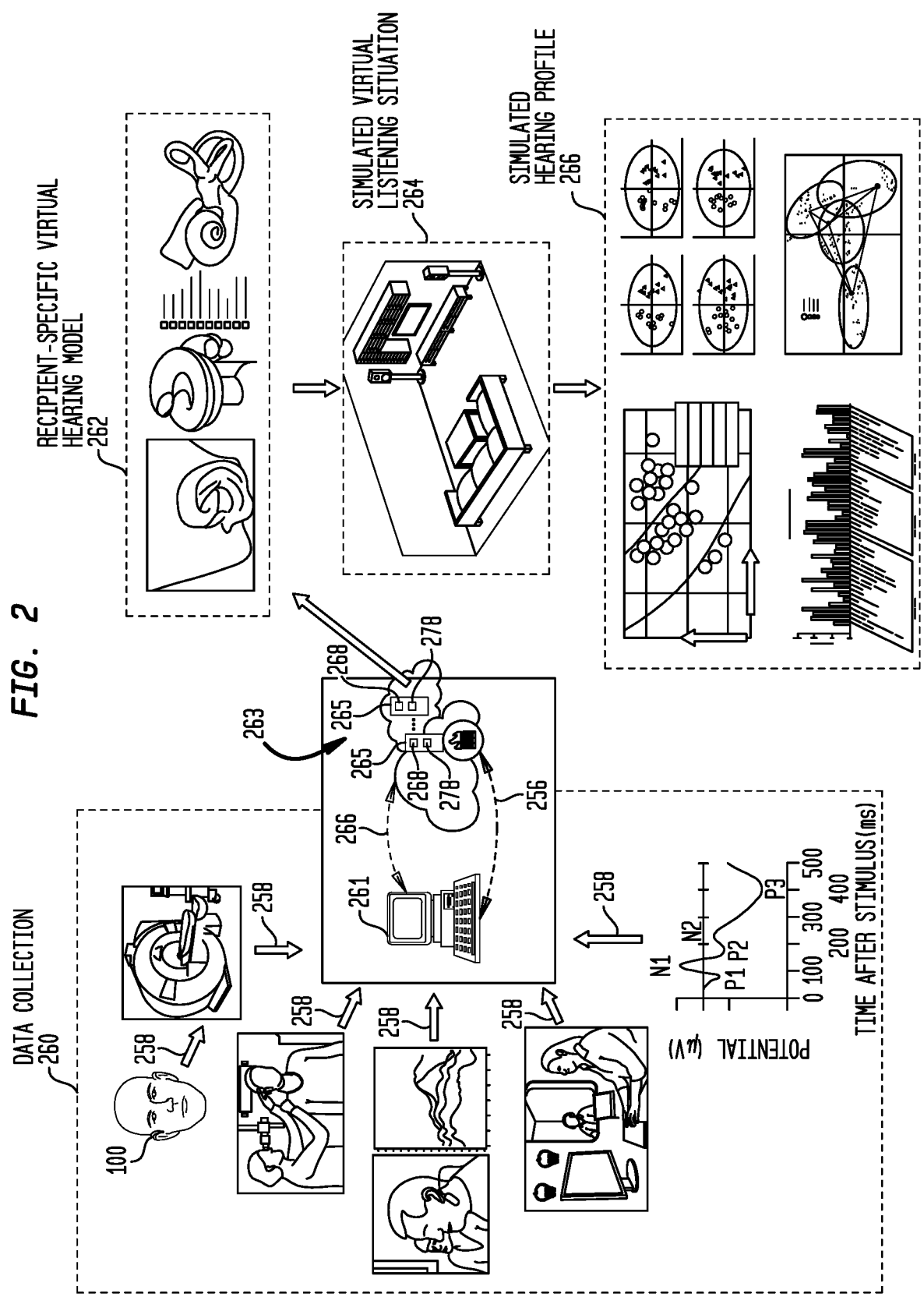
FIG. 2 is a schematic diagram illustrating operation of a portion of the techniques presented herein to generate, update, and/use a recipient-specific virtual hearing model, in accordance with certain embodiments presented herein.

FIG. 2 is a schematic diagram illustrating aspects of the techniques presented herein to generating and/or updating, as well as using, a recipient-specific virtual hearing model in accordance with certain embodiments presented herein. More specifically, shown in FIG. 2 are four (4) aspects of the techniques described herein, namely: data collection 260, a recipient-specific virtual hearing model 262, a simulated virtual listening situation 264, and a simulated hearing profile 266. For ease of description, each of these aspects are described further below with reference to cochlear implant 100 of FIGS. 1A and 1B.

Referring first to the data collection 260, this generally refers to a phase or portion of the techniques in which recipient-specific (individualized) data is gathered for subsequent use in generating or updating the recipient-specific virtual hearing model 262. More specifically, most auditory prosthesis recipients begin their hearing rehabilitation journey with some form of medical evaluation and diagnosis by an audiologist, clinician, doctor, or other medical professional (collectively and generally referred to as "clinicians" herein). For individuals who are diagnosed with mild to severe hearing loss, they may be implanted with a cochlear implant or other auditory. Individuals with less sever hearing loss may instead receive hearing aids.

During the preliminary testing phase, as well as the pre-surgery and post-surgery phases (if needed), a number of evaluations and/or measurements are performed on the recipient. These evaluations and/or measurements may take a number of different forms, such as regular health checkups, fitting sessions, image scans, hearing performance tests, etc. These different evaluations and/or measurements each generate a variety of recipient-specific "psychoacoustics data." As such herein, psychoacoustics data is data relating to, or characterizing, how the specific recipient (potentially with an auditory prosthesis) perceives sound signals (sounds). Each piece of psychoacoustics data relates to the operation/function, structure, shape, etc. of one or more of the recipient's outer, middle, and/or inner ear, and, as such, may include physical characteristics of the recipient's ear, physiological measures, nerve responses, hearing perception scores (e.g., speech in noise perception), etc. If the recipient is implanted with, or uses, an auditory prosthesis, the psychoacoustics data may characterize how the recipient perceives sounds with the aid of the auditory prosthesis. The recipient-specific psychoacoustics data could include, for example, physical measurements (e.g., optical measurements) of the recipient's ear(s) or other physical characteristics, histograms, audiograms, performance tests, age, disease states, etc.

In accordance with embodiments presented herein, the recipient-specific psychoacoustics data, represented in FIG. 2 by arrows 258, may be collected from a number of different sources in a number of different manners and locations. For example, as described elsewhere herein, the psychoacoustics data 258 may be gathered by the psychoacoustics monitoring system 154 in the cochlear implant 100. Alternatively, the psychoacoustics data 258 may be gathered via fitting systems or other computing devices in a clinic, hospital, the recipient's home, etc. FIG. 2 illustrates one example computing device 261 (e.g., computer) that is configured to gather/capture/obtain psychoacoustics data 258 in accordance with certain embodiments presented herein. As noted, it is to be appreciated that the computing device 261 is merely illustrative and that, in practice, a recipient's psychoacoustics data 258 could be gathered from a large number of different devices, locations, etc.

In accordance with embodiments presented herein, the recipient-specific psychoacoustics data 258 (e.g., captured by the computing device 261, cochlear implant 100, etc.) are collected and stored at a computing system 263 comprised of one or more computing devices 265. The one or more computing devices 265 may, as represented by arrows 266 in FIG. 2, be in wireless communication with the computing device 261, cochlear implant 100, or any other psychoacoustics data collection devices.

In certain embodiments, the computing system 263 may be a remote (e.g., cloud-based) system and the computing devices 265 may be, for example, servers. In other embodiments, the computing system 263 may be a local system and the computing devices 265 may be, for example, servers, computers, mobile computing devices, etc. In still other embodiments, the computing system 263 may include both local computing devices (e.g., a mobile computing device carried by a recipient) and remote devices (e.g., servers at a central processing location).

In certain embodiments, the cochlear implant 100 may have the capability to communicate directly with the computing system 263 (e.g., via a communications network, via a short-range wireless connection, etc.), where the computing system 263 may be a local device (e.g., mobile phone) or a remote (e.g., cloud-based) system. In such embodiments, the request for updated sound processing settings is received directly from the cochlear implant 100. However, in other embodiments, the cochlear implant 100 may rely on a local device, such as a mobile phone, to communicate with the computing system 263.

As noted, the computing system 263 (e.g., computing devices 265) is configured to store the recipient-specific psychoacoustics data 258. The computing system 263 is further configured to use the recipient-specific psychoacoustics data 258 to generate/construct the recipient-specific virtual hearing model 262. As noted above, the recipient-specific virtual hearing model 262 is an advanced and customized computing model generated from the recipient-specific psychoacoustics data 258 so as to represent how the recipient's hearing system operates, in a bilateral manner, to convert sound signals into sound perceptions. That is, the recipient-specific virtual hearing model 262 is able to receive, as inputs, representations of sounds and then estimate how the recipient is likely to perceive those represented sounds (i.e., what the recipient would likely hear if those sounds were input to the recipient's actual hearing system).

The recipient-specific virtual hearing model 262 is generated and executed at the computing system 263 by a machine-trained expert system 268 (i.e., the recipient-specific virtual hearing model 262 is generated and/or updated using an expert system implementing machine-learning algorithms and/or artificial intelligence algorithms). In certain embodiments, artificial intelligence (AI) may also be used in the generation or updating of the recipient-specific virtual hearing model 262. Since the computing system 263 is separate from the cochlear implant 100, there is potentially a large amount of processing capabilities available to execute the model based on large parameter sets. Accordingly, the computing system 263 has sufficient processing power to use the machine-trained expert system 268 and recipient-specific virtual hearing model 262 to perform advanced modelling and computer simulations in terms of how a recipient is likely to perceive various sounds.

With all the collected recipient-specific psychoacoustics data 258 (e.g., physical characteristics, physiological measures, nerve responses, etc.), the recipient-specific virtual hearing model 262 may be, in form, a holistic model of the hearing system of the recipient, covering all of the outer ear, middle ear, and inner ear systems, as well as some element of the hearing cognition in auditory cortex and brain. In certain embodiments, in addition to the recipient-specific psychoacoustics data 258, the recipient-specific virtual hearing model 262 may be generated, at least in part, based on data gathered from other recipients. For example, the recipient-specific virtual hearing model 262 could be generated or updated based on data obtained from recipients with similar types of hearing loss, with the same diseases and/or pathologies, with similar hearing profiles, with similar demographics, etc.

In accordance with embodiments presented herein, the recipient-specific psychoacoustics data 258 is collected when the recipient begins his/her rehabilitation journey and undergoes the implant surgery (i.e., generate the hearing model based on the recipient's pre-surgery and post-surgery data). In cochlear implants, a recipient generally undergoes a first fitting or "switch-on" session some period of time after the surgery. This is the first point in time in which the cochlear implant is activated and the recipient is able to use the implant to perceive sounds. Upon the first fitting/switch-on session, the recipient's hearing profile, which is a type of the recipient-specific psychoacoustics data 258, would further be uploaded to the computing system 263. At this point, the machine-trained expert system 268 generates the recipient-specific virtual hearing model 262.

The recipient-specific virtual hearing model 262 generally covers the recipient's entire hearing system, including both the left and right ears. This bilateral formation allows the impacts of various settings on the ability of the recipient to localize sound to be determined. The recipient-specific virtual hearing models present herein may also cover cases where: (1) the recipient is a unilateral recipient (e.g., hearing aid, bone conduction, cochlear implant, or other auditory prosthesis at one ear, and normal hearing in the other ear); (2) the recipient is a bimodal recipient (e.g., different types of hearing prostheses at each ear, such as a cochlear implant at one ear and a hearing aid at the other ear; or (3) the recipient is a bilateral recipient (e.g., the same type of auditory prosthesis at both ears, such as two cochlear implants), as needed.

As noted, the recipient-specific virtual hearing model 262 is built using recipient-specific psychoacoustics data 258, which includes data relating to how the cochlear implant 100 aids the recipient's perception (i.e., the estimated perception is the perception of the recipient using the cochlear implant). As such, in accordance with embodiments presented herein, the recipient-specific virtual hearing model 262 is can be used in computer simulations to select, determine, and or dynamically adjust the sound processing settings used by the cochlear implant 100 in a manner that improves the recipient's hearing perception performance.

More specifically, in accordance with embodiments presented herein, the recipient-specific virtual hearing model 262 can be used to simulate operation of the recipient's hearing system in a number of different simulated/virtual "listening situations" (i.e., the virtual hearing model is tested/simulated in a virtual listening situation). As used herein, a virtual "listening situation" is a specific set of audio circumstances that may be experienced by a recipient of an auditory prosthesis (e.g., recipient of cochlear implant 100). The set of audio circumstances forming a virtual listening situation extend beyond a simple environmental classification (e.g., "Speech," "Noise," etc.). That is, in accordance with embodiments presented herein, the simulations are performed with much more granularity and more detail than simply different "sound environments" (e.g., Noise, Speech, etc.).

For example, a virtual listening situation in accordance with embodiments presented herein may take in account recipient-specific factors, such as the person's cognitive load, age/aging, heredity attributes (e.g., related to hearing), emotional state, etc. In certain embodiments, the virtual listening situation can account for external factors, such non-verbal cues such as the tone of the voice (if there is speech), gestures, body language, etc. In certain embodiments, the virtual listening situation may include a determination of the "type" of person producing the speech. For example, a person may listen more intensively if he/she is interacting with a work supervisor, compared to when he/she is interacting with peers. In another example, a person may listen intensively when he/she is engaged in a telephone conversation since the other cues (e.g., gestures, body language, etc.) related to the message/information are not available. Oher listening situations could vary greatly and may depend on how the generated information (simulation results) will be used (e.g., listening to something just for relaxation compared to listening to something in order to learn).

Shown in FIG. 2 is an example simulated virtual listening situation 264. In accordance with the techniques presented herein, the computing system 263 includes a profile simulator 278 that simulates operation of the recipient-specific virtual hearing model 262 in a number of different virtual listening situations a number of different times. Through testing the recipient-specific virtual hearing model 262 in one or more simulated virtual listening situations, the machine-trained expert system 268 is able to learn the settings and/or adjustment for cochlear implant 100 that would introduce the best optimal hearing perception in the recipient-specific virtual hearing model 262 and, accordingly, for the actual recipient.

That is, as noted above, the recipient-specific virtual hearing model 262 inherently incorporates the operation of the cochlear implant 100 (and/or another auditory prosthesis, if present). Therefore, with each simulation iteration, the recipient-specific virtual hearing model 262 is also simulating how the recipient's cochlear implant 100 would likely perform and affect the recipient's hearing perception, in the event the recipient were to encounter a real listening situation matching the virtual listening situation. During these simulations, the performance of cochlear implant 100 is simulated using virtual/simulated sound processing settings.

In particular, in accordance with embodiments presented herein, the machine-trained expert system 268 includes a machine-learning algorithm that is trained to learn what settings and/or adjustment to operation of cochlear implant 100 would bring out the optimal hearing perception on the recipient-specific virtual hearing model 262 in a given listening situation. The machine-learning algorithm of the machine-trained expert system 268 is configured to simulate operation of the recipient-specific virtual hearing model 262 in a number of different listening situations (e.g., shopping center, restaurant, concert hall, classroom, office, special sets of spatial sound sources, etc.) with different sound processing settings in each of the different listening situations without interrupting the recipient's hearing or routine. Therefore, in various simulation iterations of the recipient-specific virtual hearing model 262, the simulated sound processing settings for the cochlear implant 100 can be changed/adjusted to determine whether the cochlear implant 100, and thus the recipient-specific virtual hearing model 262 in general, would provide better or worse sound perception for the recipient in the associated virtual listening situation. As described further below, the simulated scenarios can be, in certain examples, based on the real-time environments that the recipient is experiencing, or scenarios that the recipient has not yet experienced, but are predicted to be experienced by the recipient.

Over time, the simulation of the recipient-specific virtual hearing model 262 in different virtual listening situations generates a "simulated hearing profile" 266 for the recipient. As used herein, the simulated hearing profile 266 is a collection of simulated outputs from execution of the recipient-specific virtual hearing model 262. The recipient's simulated hearing profile 266 can be used to generate the settings (e.g., MAP) that can be instantiated (e.g., sent to, installed, and activated) at a recipient's auditory prosthesis.

For example, assume a scenario in which a system (e.g., smart home system that the recipient is using at home) detects (via sensors) that the recipient enters the laundry room to operate the washing machine. The system would initiate a connection to the cloud to obtain a simulated profile (e.g., a profile of operation of the recipient's prosthesis when operating the washing machine in the laundry room) in such a way that the settings determined to be optimal (e.g., threshold (T) levels, comfort (C) levels, etc.) are sent to the prosthesis and used to update the T and C levels at certain frequency band(s). In another example scenario, a recipient enters a library (e.g., quiet environment) and sits at a table to read, where the place he/she sits is closer to a wall or near the corner of the room (e.g., reverberation or repercussion). Based on the geographical floor location, a system (e.g., recipient's smart phone or GPS sensor) sends information to the cloud. The cloud then searches for a simulated profile where simulations have been performed in a "Quiet" environment (since the library is likely a "Quiet" sound environment) and in combination with repercussion suppression information (due to the nearness of the wall(s).

In certain embodiments, the machine-trained expert system 268 includes a rating sub-system which enables the machine-trained expert system 268 to learn what benchmark (s) should be achieved when the system is creating and/or running different simulated listening situations with the recipient-specific virtual hearing model 262. These benchmarks could be based on, for example, data obtained from a larger population of recipients. For example, the data generated from simulating virtual hearing models associated with many other recipients can be compared and correlated, with the impacts of various sound processing settings on other similar recipients in the population being analyzed to better understand how changes will best be made to the auditory prosthesis used by a given recipient.

In general, the recipient-specific virtual hearing model 262 can be updated over time based on the results of the simulations. Additionally, the recipient-specific virtual hearing model 262 can be updated, again over time, as new psychoacoustic data is received throughout the lifetime of the recipient from, for example, psychoacoustics monitoring system 154, computing system 261, and/or other sources. This new recipient-specific psychoacoustics data 258 may be, for example, from fitting session data, data from the post-surgery MRI or other imaging scans, data from the regular health check-ups, physiological measures at the beginning of each week/month, background objective measures taken from the running devices, device setting changes by the recipient, device usage logs, etc. If new psychoacoustic data is received, the recipient-specific virtual hearing model 262 can be (e.g., periodically) re-simulated in different listening situations and the simulated hearing profile 266 can accordingly be updated.

As noted above, the computing system 263 and, more specifically the machine-trained expert system 268, operates in conjunction with the psychoacoustics monitoring system 154 in the cochlear implant 100. The psychoacoustics monitoring system 154 is generally configured to monitor (e.g., continuously) the recipient's real-time ambient environment and provide indications of a recipient's "expected listening situation" to the machine-trained expert system 268. As used herein, a recipient's "expected listening situation" is a specific set of audio circumstances that recipient has encountered, or is likely to encounter in the near future. As noted above, similar to the virtual listening situation, the set of audio circumstances forming an expected listening situation extend beyond a simple environmental classification (e.g., "Speech," "Noise," etc.) and also include details such as recipient-specific factors, external factors, etc.

In accordance with certain embodiments presented herein, the recipient's expected listening situation is determined from the sound signals received at the one or more input devices 134 of cochlear implant 100. In particular, the cochlear implant 100 (e.g., psychoacoustics monitoring system 154) is configured to provide the computing system 263 and, more specifically the machine-trained expert system 268, with "listening situation data," which represents an expected listening situation for the auditory prosthesis. The listening situation data may include, for example, a classification of the sound environment (e.g., "Noise," "Speech," etc.), SNR, average speech and average noise levels, the rough spatial distribution of speech and noise sources, the dynamic range and spectral characteristics of the various components of the auditory scene, other characteristics of the surrounding noise environment (e.g., background music distribution and level), etc.

In certain embodiments, when the characteristics of the recipient's expected listening situation are found to be closely matched to a simulated listening situation, the machine-trained expert system 268 can select the associated sound processing settings (e.g., processing algorithm, T and C levels, noise masker, activation/deactivation of particular operational features, the gain setting on a particular electrode or groups of electrodes, the delay timing alignment between the acoustic and electrical sound paths, the chip processor power control/consumption/speed, etc.) determined to be most optimal in that matched simulated listening situation and push these onto the recipient's cochlear implant 100 for instantiation and use. In certain examples, the machine-trained expert system may even suggest changes outside of the prosthesis itself. For instance, for a recipient ho has tinnitus, besides applying the noise masker, the expert system may advise the recipient to turn on a device/speaker to broadcast or stream over the soft natural sound to soothe the tinnitus.

For example, in accordance with embodiments presented herein, the psychoacoustics monitoring system 154 in cochlear implant 100 can be configured to determine that the recipient is experiencing, or is likely to experience, a certain listening situation. The psychoacoustics monitoring system 154 can provide data representing an expected listening situation to the machine-trained expert system 268, which in turn can select a set of sound processing settings (determined based on the recipient-specific virtual hearing model 262 analysis in different simulated environments) and provide these selected set of sound processing settings to the cochlear implant 100 for instantiation and use (e.g., for use by sound processing module 152, etc.). For example, the machine-learning algorithm in the machine-trained expert system 268 can determine the most likely matched virtual listening situation (based on the data received from the cochlear implant 100). Using the matched virtual listening situation, the machine-learning algorithm can select the most optimal set of sound processing settings for the cochlear implant 100 in the expected listening situation. Further examples of such real-time determination of auditory prosthesis settings are described in further detail below.

Since the recipient-specific virtual hearing model 262 represents the recipient's natural auditory system, from the diagnostic perspective, clinicians could use the model to predict and understand the physical potential capability and limitations of the recipient's hearing perception. Effectively, by looking at the recipient's virtual hearing model 262 that will be updated continuously as the recipient is getting older, potentially the shortcomings of the auditory system could be noticed well in advance. As such, diagnostic, rehabilitation, and other exercises that could be planned accordingly. For instance, the effect of a specific rehabilitation strategy, or sound processing settings change, could be simulated prior to being applied, and the likely effect thereof on the hearing performance can be predicted.

In certain embodiments, the proposed system could have the advantage of keeping, comparing and/or even deducing (with the usage of artificial intelligence) what the recipient's virtual hearing model 262 could be like in the future (e.g., in one year, in five years, in ten years, etc.). For someone who is prone to suffer from ear discomfort (e.g., ear barotrauma) due to pressure changes, the recipient-specific virtual hearing model 262 could factor in such an item and simulate the environmental changes in such a way to let the recipient and/or the clinician be aware of the situation so that customized precautions could be taken if the recipient is going to travel or move to a location at which he/she would experience such pressure changes. The modelling can be based on similar trends observed by other recipients in the population that have similar or analogous simulated hearing profiles.

Another application of the recipient-specific virtual hearing model 262 could be extended and applied onto the rehabilitation area. Most of the existing rehabilitation programs require extensive time from both the recipient and his/her clinician to go through several trail-and-error sessions in order to figure out the optimal rehabilitation for the recipient. The recipient may or may not be able to achieve the best rehabilitation based on these subjective sessions. In accordance with embodiments presented herein, the recipient-specific virtual hearing model 262 could provide another tool that the clinician (or the whole clinic) could use to identify an optimal individualized rehabilitation program/plan for the recipient (e.g., advanced modelling and computer simulations to select customized rehabilitation exercises for the recipient).

For example, the recipient-specific virtual hearing model 262 may be used to select customized rehabilitation exercises for the recipient. In certain embodiments, with supplementary information (such as age, occupation, geographical location, life habits, etc.), a large number of models with respect to different individuals in the population could be constructed. These models could be further grouped into different user groups. For instance, a user group that shows the normal hearing at a certain age range, a user group containing the characteristics of tinnitus, a user group showing the characteristics or impact upon taking certain medication, and so on. With all these user groups, the model of an individual could be used and compared to the characteristics of the models of those user groups.

In such examples, the models may show that, because of the hearing loss, there is a likelihood for an individual to experience high levels of anxiety resulting in loss of concentration, inability to remember conversations, and even could not listen to another party. In this case, the system would select exercises (specially focused on sounds) to stimulate the person's cognitive function or choose the games so as to help the individual to train to remember more, concentrate better, think sharper, etc.

Figure 3:
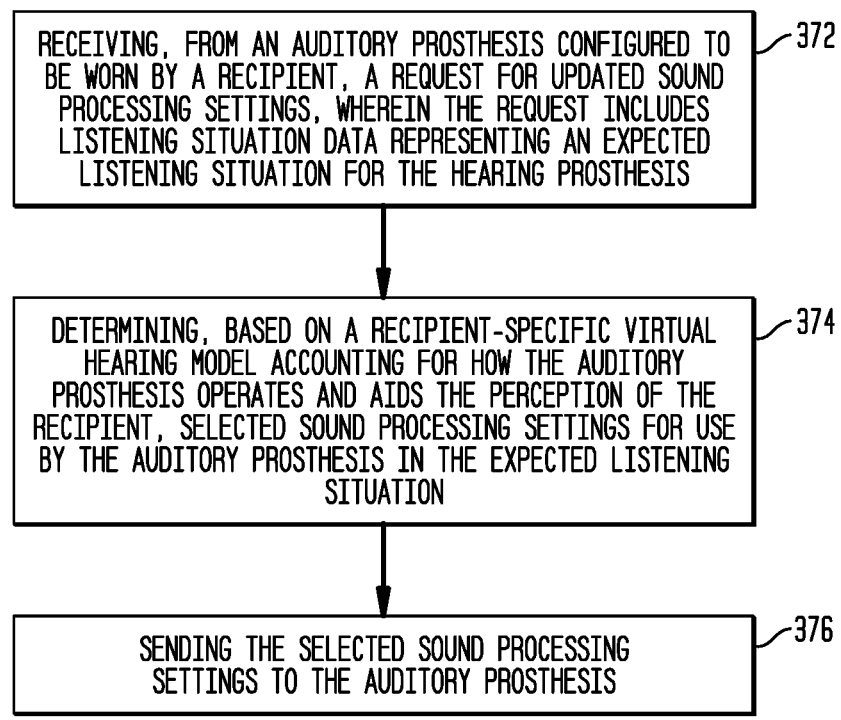
in FIG. 3 is a flowchart of a method, in accordance with certain embodiments presented herein.

As described above, in accordance with embodiments presented herein, a recipient-specific virtual hearing model can be used in real-time to dynamically select/adjust (optimize) the settings of a recipient's auditory prosthesis. FIG. 3 is a flowchart illustrating an example method 370 for dynamic or real-time use of a recipient-specific virtual hearing model in accordance with embodiments presented herein. For ease of illustration, the method 370 FIG. 3 will be described with reference to cochlear implant 100 of FIGS. 1A and 1B and the computing system 263 of FIG. 2. However, it is to be appreciated that the method of FIG. 3 may be implemented with other auditory prostheses, computing systems, etc.

More specifically, method 370 begins at 372 where the computing system 263 receives, from cochlear implant 100, a request for updated sound processing settings. The request received from cochlear implant 100 includes the listening situation data representing expected listening scenario for the cochlear implant. In accordance with embodiments presented herein, the "expected" listing situation can be a current/present listening scenario of the cochlear implant 100, or an estimated/predicted future listing scenario.

In general, the expected listening situation for the cochlear implant 100 is determined by the psychoacoustics monitoring system 154 based, at least in part, on the sound signals received at the cochlear implant. More specifically, in one example, a system may be provided in which a structure (e.g., table) is defined to indicate the basic characteristics or patterns of different listening situation. For instance, there could be a likelihood or reference score defined in the system. In practice, the information relating to such characteristics could be collected, monitored, and tracked in in real time. Through analyzing the continuously collected characteristics relating to the surroundings (related to the listening situation as well as the external one such as the location of the recipient), the system will build a likelihood reference and/or probability score. When that probability score (based on all the relevant combined characteristics) is getting close to the reference score, the system would know that the recipient is situated in the expected listening situation.

For example, in certain embodiments, the cochlear implant 100 is configured to sample and classify the sound environment (e.g., an environmental classifier the generates sound classification information/data that is used to determine the expected listening situation), as well as to determine other sound parameters, such as average speech and average noise levels, the rough spatial distribution of speech and noise sources, the dynamic range and spectral characteristics of the various components of the auditory scene, other characteristics of the surrounding noise environment (e.g., background music distribution and level), etc.

In certain embodiments, the cochlear implant 100 generates the request for the updated sound processing settings automatically (i.e., without involvement by the recipient). The automated request for the updated sound processing settings could be sent by the cochlear implant 100 in response to detection of a number of different conditions (e.g., detection of new sound environment or specific sound parameters, at certain points in time, etc.). In other embodiments, the cochlear implant 100 generates the request for the updated sound processing settings in response to one or more user inputs received at the cochlear implant 100 or another device (e.g., mobile phone, remote control, or other mobile computing device in communication with the cochlear implant 100).

Returning to the example of FIG. 2, in response to the request from cochlear implant 100, at 374 the computing system 263 determines, based on the virtual hearing model 263 representing operation of the recipient's hearing system, selected sound processing settings for use by the cochlear implant 100 in the expected listening situation. At 376, the selected sound processing settings are sent to the cochlear implant 100 for instantiation and subsequent use by the cochlear implant 100. That is, once the selected sound processing settings are received at the cochlear implant 100, the cochlear implant 100 installs the selected sound processing settings and begins processing sound signals using those settings.

The computing system 263 can use the virtual hearing model 262 to determine the selected sound processing settings in a number of different manners. For example, as noted above, the computing system 263 is configured to simulate the virtual hearing model 262 in different virtual listening situations (i.e., to predict how the recipient's hearing system, as aided by cochlear implant 100, would perceive sounds in different scenarios having different acoustical properties, different noise levels, etc.). In certain embodiments, these simulations can be pre-run so as cover a variety of different listening situations. In these embodiments, when the request for updated sound processing setting is received from the cochlear implant 100, the computing system 263, more specifically machine-trained expert system 268, determines which of the pre-performed simulated virtual listening situations most closely matches the expected listening situations. The machine-trained expert system 268 that selects, as the selected sound processing settings, the simulated sound processing settings that performed best in the most closely matching simulated virtual listening situation. That is, the most optimal sound processing settings for each simulated listening situation are stored in the computing system 263. Upon receiving the request for updated sound processing from the cochlear implant 100, the machine-trained expert system 268 matches the expected listening situation to a simulated listening situation and then selects, as the selected sound processing parameters, the sound processing settings determined to be most optimal (for the recipient-specific virtual hearing model 262 and thus for the recipient) in the associated simulated listening situation.

The above illustrates an example in which the data indicating the expected listening situation is used by the machine-trained expert system 268 to identify a similar/analogous simulated listening situation and the sound processing parameters associated therewith. In other embodiments, the data indicating the expected listening situation can be used, in real-time, to build or select a listening environment for simulation and accordingly determine the selected sound processing parameters. That is, in these embodiments, the machine-trained expert system 268 uses the data included in the request from the cochlear implant 100 to create, build, select, etc. a simulated listening situation that matches the expected listening situation of the recipient of cochlear implant 100. The machine-trained expert system 268 then runs real-time simulations for the recipient-specific virtual hearing model 262, and thus for the recipient, in the selected simulated listening situation to determine optimal sound processing settings for the cochlear implant 100 in the expected listening situation. As noted, upon completion of this analysis, the selected sound processing settings are provided to the cochlear implant 100.

As noted above, the computing system 263 can use the recipient-specific virtual hearing model 262 in a number of different manners to determine the selected sound processing settings for cochlear implant 100. As such, it is to be appreciated that the above two techniques for determining the selected sound processing settings are merely illustrative and that embodiments presented herein may use other techniques for selection of the sound processing settings for cochlear implant 100 or another auditory prosthesis.

To facilitate further understanding of the techniques presented, provided below are several examples of the real-time applicability of a recipient-specific virtual hearing model to selection of sound processing settings. For ease of illustration, these examples are again described with reference to cochlear implant 100 of FIGS. 1A and 1B and the computing system 263 of FIG. 2. However, it is to be appreciated that similar techniques may be implemented with other auditory prostheses, computing systems, etc.

In one example, the recipient of cochlear implant 100 enters a cocktail party (i.e., an expected listening environment). The cochlear implant 100 is configured to sample and classify the sound environment (e.g., an environmental classifier determines that the recipient is in a "Speech+Noise" environment), as well as determine other sound parameters, such as average speech and average noise levels, the rough spatial distribution of speech and noise sources, the dynamic range and spectral characteristics of the various components of the auditory scene, other characteristics of the surrounding noise environment (e.g., background music distribution and level), etc. This information, sometimes referred to herein as the listening situation data, represents the expected listening situation (i.e., cocktail party) for the cochlear implant 100. As noted, the listening situation data can be communicated to the machine-trained expert system 268 in computing system 263. The machine-trained expert system 268 is configured to then run simulations on the hearing perception of the recipient in the expected listening situation (i.e., cocktail party) and determine the optimal sound processing settings for this specific listening situation. These settings then be communicated immediately to the recipient, in real-time, to adjust the cochlear implant 100 in an optimal manner.

In accordance with embodiments herein, once an expected listening situation has been encountered by the recipient, the associated sound processing settings selected for use therein by machine-trained expert system 268 can be added to a database associated with the recipient. As such, these settings can be re-applied the next time the recipient is in this or a similar listening situation without performing simulations and/or only performing a validation process. Further, this expected listening situation and associated sound processing settings could be added to a large, global database, to help fine-tune the fitting process and/or be used by other recipients when they are in similar environments.

In another illustrative example, the recipient of cochlear implant 100 enters a concert hall to listen to a performance. A concert hall is a particularly unusual listening situation for a recipient in that it with likely include significant reverberation, important harmonics, and various directional sources of information and noise. In accordance with embodiments presented herein, the psychoacoustics monitoring system 154 in the cochlear implant 100 is configured to sample the auditory environment to gather the listening situation data. In certain examples, the listening situation data can be supplemented with auxiliary environmental data from alternate sources, such as a database of sound locations, information on the performance and/or the specific venue, occupancy information, etc. obtained at computing system 263 from one or more auxiliary sources (e.g., other computing systems). Again, using the listening situation data and, in certain examples the auxiliary environmental data, the machine-trained expert system 268 is configured to run simulations on the hearing perception of the recipient in the expected listening situation (i.e., concert hall) and determine the optimal sound processing settings for this specific listening situation. These settings then be communicated immediately to the recipient, in real-time, to adjust the cochlear implant 100 in order to improve the perception and enjoyment of the concert for the recipient.

In another example, a recipient may take a bush or nature walk where the auditory environment experienced by the recipient may be quite different from what the recipient experiences in everyday life (e.g., far less auditory reflections and a background 'noise' that really isn't noise and forms somewhat part of the experience of being in the bush). In accordance with embodiments presented herein, the psychoacoustics monitoring system 154 in the cochlear implant 100 is configured to sample the auditory environment to gather the listening situation data indicating the recipient is in this specific listening situation. Again, using the listening situation data, the machine-trained expert system 268 is configured to run simulations on the hearing perception of the recipient in the expected listening situation (i.e., nature walk) and determine the optimal sound processing settings for this specific listening situation. These settings then be communicated immediately to the recipient, in real-time, to adjust the cochlear implant 100 in order to improve the perception and enjoyment of the recipient while on the nature walk.

The above specific examples are merely illustrative to show that the techniques presented herein could be used in any of a number of different circumstances to determine updated sound processing settings for cochlear implant 100 or another auditory prosthesis. The above examples also illustrate that the techniques presented herein are able to function somewhat like an advanced classifier, where the sound processing can be adapted based on a specific listening situation, with far greater adaptability and granularity than simply using an on-board environmental classifier. As such, building on the previous examples, in certain embodiments, the machine-trained expert system 268 can use the recipient-specific virtual hearing model 262 to continually run simulations based on the listening situations experienced by the recipient. The machine-trained expert system 268 could then adjust the psychoacoustics monitoring system 154 and/or the environmental classifier in the cochlear implant 100 for the specific recipient and push this on to the recipient's sound processor. This can happen regularly or even continuously in real-time, based on the listening situations experienced by the recipient.

In further embodiments, the psychoacoustics monitoring system 154 in the cochlear implant 100 could itself include a machine-learning system executing a recipient-specific virtual hearing model (e.g., implemented on an embedded AI chip). For example, the remote machine-trained expert system 268 could push/install a copy of the recipient-specific virtual hearing model 262 at the cochlear implant 100. The cochlear 100 may be the complete virtual hearing model 262 or a modified version of the virtual hearing model optimized to run in a lower-power environment. In these embodiments, the copy of the recipient-specific virtual hearing model 262 could be used, in a similar manner as described above with reference to the recipient-specific virtual hearing model 262 running in computing system 263, to select sound processing settings for the cochlear implant 100 (e.g., run simulations in virtual listening situation to, via a machine-learning algorithm, determine optimal settings for an expected listening situation). Over time, the machine-trained expert system 268 could push changes made to the recipient-specific virtual hearing model 262 to the psychoacoustics monitoring system 154 to control and alter how the embedded machine-learning system learns and adapts. In this way, an embedded machine-learning system is trained and updated regularly by a more powerful, cloud-based machine-learning system.

In other words, in these examples a low power machine-learning and/or artificial intelligence algorithm is embedded in cochlear implant 100 (e.g., as part of psychoacoustics monitoring system 154). The more powerful machine-trained expert system 268 in computing system 263 (e.g., on a mobile phone, computer, server, etc.) is used to train the embedded system for the recipient based on their listening situations and simulated hearing profile(s). At a regular basis, the embedded system, including the copy of the recipient-specific virtual hearing model 262, can be updated by the machine-trained expert system 268, thereby providing improved performance without requiring the level of processing on the cochlear implant 100 as required to train the more powerful machine-trained expert system 268 in computing system 263.

Figure 4:
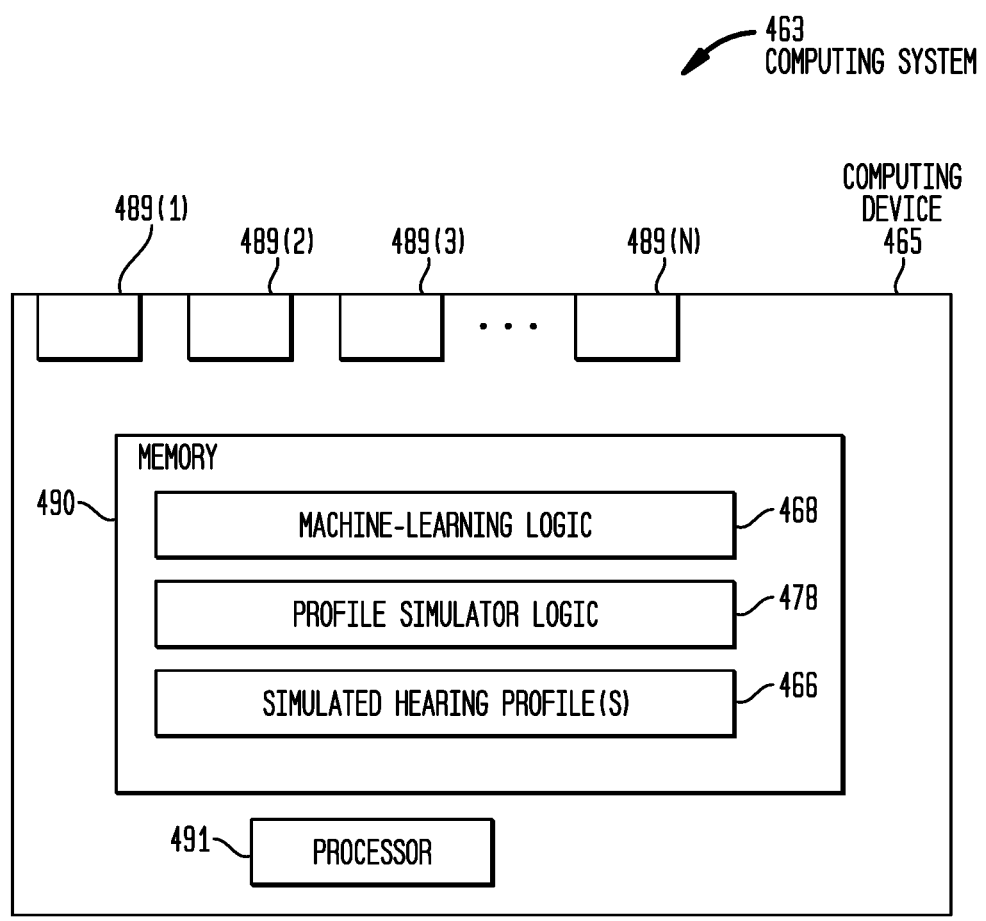
FIG. 4 is a block diagram of a computing system configured to implement aspects of the presented techniques, in accordance with certain embodiments presented herein.

As noted above, aspects of the techniques presented herein may be implemented on a local or remote computing system comprising one or more computing devices. FIG. 4 is functional block diagram of an example computing system 463 configured to implement aspects of the techniques presented herein. In the example of FIG. 4, the computing system 463 includes a single computing device 465. It is to be appreciated that this implementation is merely illustrative and that computing system in accordance with embodiments presented herein may be formed by one or a plurality of different computing devices. As such, it is to be appreciated that, in certain embodiments, the components shown in FIG. 4 may be implemented across multiple computing devices.

In FIG. 4, the computing device 465 comprises a plurality of interfaces/ports 489(1)-489(N), a memory 490, and one or more processors 491. Although not shown in FIG. 4, the computing device 465 could also include a user interface, display screen, etc., depending on the type of computing device used to implement the techniques presented herein. The interfaces 489(1)-489(N) may comprise, for example, any combination of network ports (e.g., Ethernet ports), wireless network interfaces, Universal Serial Bus (USB) ports, Institute of Electrical and Electronics Engineers (IEEE) 1394 interfaces, PS/2 ports, etc. Interfaces 289(1)-289(N) may be configured to transmit/receive signals via a wired or wireless connection (e.g., telemetry, Bluetooth, etc.).

Memory 490 includes machine-learning logic 468, profile simulator logic 478, and one or more simulated hearing profiles 466. Memory 490 may comprise read only memory (ROM), random access memory (RAM), magnetic disk storage media devices, optical storage media devices, flash memory devices, electrical, optical, or other physical/tangible memory storage devices. The one or more processors 491 are, for example, microprocessors or microcontrollers that executes instructions for the machine-learning logic 468 and the profile simulator logic 478. Thus, in general, the memory 490 may comprise one or more tangible (non-transitory) computer readable storage media (e.g., a memory device) encoded with software comprising computer executable instructions and when the software is executed (by the one or more processors 491) it is operable to perform all or part of the presented techniques. For example, the machine-learning logic 468 may be executed by the one or more processors 491 to, for example, perform the techniques described above with reference to machine-trained expert systems, such as machine-trained expert system 268. The profile simulator logic 478 may be executed by the one or more processors 491 to, for example, perform the techniques described above with reference to a profile simulator, such as profile simulator 278.

Figure 5:
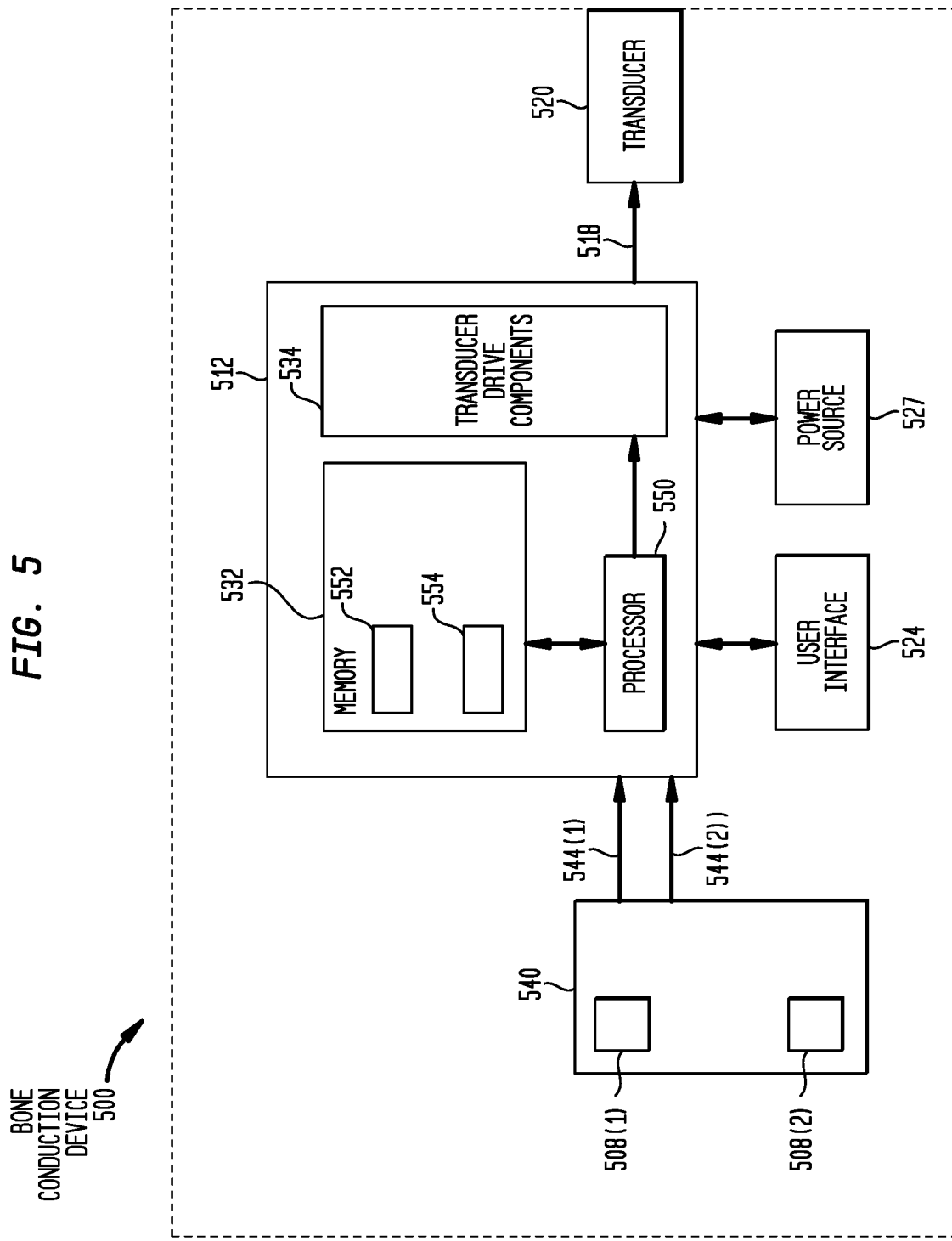
FIG. 5 is a functional block diagram illustrating a bone conduction device, in accordance with certain embodiments presented herein.

Merely for ease of description, the techniques presented herein have primarily been described herein with reference to one illustrative auditory/hearing prosthesis, namely a cochlear implant. However, it is to be appreciated that the techniques presented herein may also be used with a variety of other types of devices, including other auditory prostheses. For example, the techniques presented herein may be implemented in, for example, acoustic hearing aids, auditory brainstem stimulators, bone conduction devices, middle ear auditory prostheses, direct acoustic stimulators, bimodal auditory prosthesis, bilateral auditory prosthesis, etc. FIG. 5, in particular, is a functional block diagram of one example arrangement for a bone conduction device 500 configured to implement embodiments presented herein.

Bone conduction device 500 comprises a microphone array 540, an electronics module 512, a transducer 520, a user interface 524, and a power source 527.

The microphone array 540 comprises first and second microphones 508(1) and 508(2) configured to convert received sound signals (sounds) into microphone signals 544(1) and 544(2). The microphone signals 544(1) and 544(2) are provided to electronics module 512. In general, electronics module 512 is configured to convert the microphone signals 544(1) and 544(2) into one or more transducer drive signals 518 that activate transducer 520. More specifically, electronics module 512 includes, among other elements, at least one processor 550, a memory 532, and transducer drive components 534.

The memory 532 includes sound processing logic 552 and psychoacoustics monitoring logic 554. Memory 532 may comprise read only memory (ROM), random access memory (RAM), magnetic disk storage media devices, optical storage media devices, flash memory devices, electrical, optical, or other physical/tangible memory storage devices. The at least one processor 550 is, for example, a microprocessor or microcontroller that executes instructions for the sound processing logic 552 and psychoacoustics monitoring logic 554. Thus, in general, the memory 532 may comprise one or more tangible (non-transitory) computer readable storage media (e.g., a memory device) encoded with software comprising computer executable instructions and when the software is executed (at least one processor 550) it is operable to perform aspects of the techniques presented herein.

Transducer 520 illustrates an example of a stimulator unit that receives the transducer drive signal(s) 518 and generates stimulation (vibrations) for delivery to the skull of the recipient via a transcutaneous or percutaneous anchor system (not shown) that is coupled to bone conduction device 500. Delivery of the vibration causes motion of the cochlea fluid in the recipient's contralateral functional ear, thereby activating the hair cells in the functional ear.

Similar to cochlear implants, bone conduction devices and/or other auditory prosthesis operate in accordance with a number of sound processing settings. As such, in accordance with embodiments of FIG. 5, a virtual hearing model may be generated for the recipient of bone conduction device 500 in a computing system (e.g., system 263, system 463, etc.) based on recipient-specific psychoacoustics data captured from the bone conduction device 500 (e.g., via execution of psychoacoustics monitoring logic 554 by at least one processor 550) or from another device.

Similar to the above embodiments, simulations may be performed using this virtual hearing model in a number of different virtual listening situations to generate a simulated hearing profile for the recipient of bone conduction device 500. Subsequently, the psychoacoustics monitoring logic 554 may, when executed by the at least one processor 550, generate a request to the computing system for a set of updated sound processing for use by the bone conduction device 500 in an expected listening situation. The computing system may then determine, based on the virtual hearing model representing operation of the recipient's hearing system, selected sound processing settings for use by the bone conduction device in the expected listening situation and send the selected sound processing settings to bone conduction device 500 for instantiation.

FIG. 6 is a flowchart of a method 692, in accordance with embodiments presented herein. Method 692 begins at 693 where a virtual hearing model is generated based on recipient-specific psychoacoustics data. Once generated, the virtual hearing model is a holistic model of the hearing system of a recipient of an auditory prosthesis, and the virtual hearing model accounts for, in a bilateral manner, operation of each of the outer ears, middle ears, and inner ear systems of the recipient, as well as the hearing cognition in auditory cortex and brain of the recipient, and how the auditory prosthesis operates and aids the perception of the recipient. At 694, the virtual hearing model is used to determine selected sound processing settings for use by the auditory prosthesis. At 695, the selected sound processing settings are instantiated (e.g., sent to, installed, and activated) at the auditory prosthesis.

It is to be appreciated that the above described embodiments are not mutually exclusive and that the various embodiments can be combined in various manners and arrangements.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method, comprising:
at a computing system:
receiving a request for sound processing settings for a hearing device configured to be worn by a recipient, wherein the request includes listening situation data representing an expected listening situation for the hearing device;

determining, based on a model of an auditory system of the recipient, selected sound processing settings for use by the hearing device in the expected listening situation; and sending the selected sound processing settings to the hearing device.

2. The method of claim 1, wherein the model of the auditory system of the recipient accounts for, in a bilateral manner, operation of each of the outer ears, middle ears, and inner ear systems of the recipient, as well as the hearing cognition in the auditory cortex and the brain of the recipient, and how the hearing device operates and aids a perception of the recipient.

3. The method of claim 1, wherein determining the selected sound processing settings for use by the hearing device in the expected listening situation comprises:
iteratively performing simulations for the model in at least one listening situation matching the expected listening situation;
in each iteration, adjusting a simulated operation of the hearing device in the model to account for different sound processing settings of the hearing device; and
determining, as the selected sound processing settings for use by the hearing device, a set of sound processing settings estimated to provide a selected hearing perception for the recipient in the at least one listening situation matching the expected listening situation.

4. The method of claim 3, further comprising:
prior to receiving the request from the hearing device, iteratively performing simulations for the model in a plurality of different listening situations, wherein at least one of the plurality of different listening situations comprises the at least one listening situation matching the expected listening situation;
following receipt of the request from the hearing device, identifying the at least one listening situation matching the expected listening situation; and
determining, as the selected sound processing settings for use by the hearing device, a set of sound processing settings previously estimated to provide a selected hearing perception for the recipient in the at least one listening situation matching the expected listening situation.

5. The method of claim 3, further comprising:
following receipt of the request from the hearing device, generating, based on listening situation data, the at least one listening situation matching the expected listening situation;
iteratively performing simulations for the model of the auditory system of the recipient in the at least one listening situation matching the expected listening situation;
in each iteration, adjusting the simulated operation of the hearing device in the model to account for different sound processing settings of the hearing device; and
determining, as the selected sound processing settings for use by the hearing device, a set of sound processing settings estimated to provide a selected hearing perception for the recipient in the at least one listening situation matching the expected listening situation.

6. The method of claim 3, wherein adjusting the simulated operation of the hearing device in the model in each iteration comprises:
adjusting the simulated operation of the hearing device in the model using a machine-learning algorithm.

7. The method of claim 3, wherein adjusting the simulated operation of the hearing device in the model in each iteration comprises:
adjusting the simulated operation of the hearing device in the model using an artificial intelligence algorithm.

8. The method of claim 1, further comprising:
generating the model based on recipient-specific psychoacoustics data.

9. The method of claim 1, further comprising:
generating the model based on psychoacoustics data gathered from one or more selected populations of hearing device recipients.

10. A method, comprising:
generating, based on recipient-specific psychoacoustics data, a hearing model, wherein the hearing model is a model of an auditory system of a recipient of a hearing device, and wherein the hearing model accounts for, in a bilateral manner, operation of each of the outer ears, middle ears, and inner ear systems of the recipient, as well as a hearing cognition in an auditory cortex and brain of the recipient, and how the hearing device operates and aids a perception of the recipient;
using the hearing model to determine selected sound processing settings for use by the hearing device; and
instantiating the selected sound processing settings at the hearing device.

11. The method of claim 10, wherein using the hearing model to determine selected sound processing settings for use by the hearing device comprises:
receiving, from the hearing device, a request for sound processing settings, wherein the request includes listening situation data representing an expected listening situation for the hearing device;
iteratively performing simulations for the hearing model in at least one listening situation matching the expected listening situation;
in each iteration, adjusting a simulated operation of the hearing device in the hearing model to account for different sound processing settings of the hearing device; and
determining, as the selected sound processing settings for use by the hearing device, a set of sound processing settings estimated to provide a selected hearing perception for the recipient in the at least one listening situation matching the expected listening situation.

12. The method of claim 11, further comprising:
prior to receiving the request from the hearing device, iteratively performing simulations for the hearing model in a plurality of different listening situations, wherein at least one of the plurality of different listening situations comprises the at least one listening situation matching the expected listening situation;
following receipt of the request from the hearing device, identifying the at least one listening situation matching the expected listening situation; and
determining, as the selected sound processing settings for use by the hearing device, a set of sound processing settings previously estimated to provide a selected hearing perception for the recipient in the at least one listening situation matching the expected listening situation.

13. The method of claim 11, further comprising:
following receipt of the request from the hearing device, generating, based on listening situation data, the at least one listening situation matching the expected listening situation;

iteratively performing simulations for the hearing model in the at least one listening situation matching the expected listening situation;

in each iteration, adjusting the simulated operation of the hearing device in the hearing model to account for different sound processing settings of the hearing device; and determining, as the selected sound processing settings for use by the hearing device, a set of sound processing settings estimated to provide a selected hearing perception for the recipient in the at least one listening situation matching the expected listening situation.

14. The method of claim 10, further comprising:

generating the hearing model based on psychoacoustics data gathered from one or more selected populations of hearing device recipients.

15. The method of claim 10, wherein instantiating the selected sound processing setting at the hearing device includes:

sending the selected sound processing setting to the hearing device.

16. One or more non-transitory computer readable storage media comprising instructions that, when executed by a processor, cause the processor to:

obtain a recipient-specific model of a perceptual system of a recipient of an implantable medical device;

obtain situation data representing expected future use situations for the implantable medical device; and determine settings for use by the implantable medical device in the expected future use situations based on the situation data and the recipient-specific model.

17. The one or more non-transitory computer readable storage media of claim 16, further comprising instructions operable to:

provide the settings to the implantable medical device.

18. The one or more non-transitory computer readable storage media of claim 16, wherein the implantable medical device is a hearing device, and wherein the situation data comprises listening situation data representing one or more expected listening situations.

19. The one or more non-transitory computer readable storage media of claim 16, wherein the implantable medical device is an hearing device, and wherein the recipient-specific model is a model of an auditory system of the recipient accounting for, in a bilateral manner, operation of each of the outer ears, middle ears, and inner ear systems of the recipient, as well as the hearing cognition in the auditory cortex and the brain of the recipient, and how the hearing device operates and aids the perception of the recipient.

20. The one or more non-transitory computer readable storage media of claim 16, wherein the instructions operable to determine the settings for use by the implantable medical device in the expected future use situations comprise instructions operable to:

iteratively perform simulations for the recipient-specific model in at least one situation matching at least one expected future use situation;

in each iteration, adjust a simulated operation of the implantable medical device in the recipient-specific model to account for different settings of the implantable medical device; and determine, as the settings for use by the implantable medical device, a set of settings estimated to provide a selected perception for the recipient in the at least one situation matching the at least one expected future use situation.

21. The one or more non-transitory computer readable storage media of claim 20, wherein the instructions operable to adjust the simulated operation of the implantable medical device in the recipient-specific model in each iteration comprise instructions operable to:

adjust the simulated operation of the implantable medical device in the recipient-specific model using a machine-learning algorithm.

22. The one or more non-transitory computer readable storage media of claim 21, wherein the instructions operable to adjust the simulated operation of the implantable medical device in the recipient-specific model in each iteration comprise instructions operable to:

adjust the simulated operation of the implantable medical device in the recipient-specific model using an artificial intelligence algorithm.

* * * * *